(12) United States Patent
Bodner et al.

(10) Patent No.: US 12,728,194 B2
(45) Date of Patent: Sep. 8, 2026

(54) IMPLANTABLE MICROSPHERE RESERVOIR

(71) Applicant: Medtronic, Inc., Minneapolis, MN (US)

(72) Inventors: Jeffrey P. Bodner, Plymouth, MN (US); Touby A. Drew, Golden Valley, MN (US); Nicholas Whitehead, Lake Elmo, MN (US); J. Michael Gray, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 515 days.

(21) Appl. No.: 17/573,724

(22) Filed: Jan. 12, 2022

(65) Prior Publication Data

US 2022/0257854 A1 Aug. 18, 2022

Related U.S. Application Data

(60) Provisional application No. 63/148,661, filed on Feb. 12, 2021.

(51) Int. Cl.
*A61M 5/14* (2006.01)
*A61K 9/16* (2006.01)
(Continued)

(52) U.S. Cl.
CPC ............ *A61M 5/1409* (2013.01); *A61K 9/16* (2013.01); *A61M 5/14276* (2013.01);
(Continued)

(58) Field of Classification Search
CPC ........... A61M 2005/14284; A61M 2039/0261; A61M 2202/0007; A61M 2202/04; A61M 2205/50; A61M 39/0247; A61M 5/1409; A61M 5/14276; A61M 5/16827; A61M 2039/0211; A61M 2039/0235; A61M 2039/0238; A61M 2039/0241; A61M 2039/0244; A61M 2205/04; A61M 2205/18; A61M 2205/3303; A61M 2205/3334; A61M 2205/581;
(Continued)

(56) References Cited

U.S. PATENT DOCUMENTS

| | | | | |
|---|---|---|---|---|
| 4,936,831 A * | 6/1990 | Jaehrling | A61M 5/165 | 210/489 |
| 5,417,663 A * | 5/1995 | Slettenmark | A61M 5/14276 | 604/126 |
| 6,458,118 B1 * | 10/2002 | Lent | A61M 5/14276 | 604/890.1 |
| 2004/0230182 A1 * | 11/2004 | Heruth | A61M 5/14276 | 604/891.1 |

(Continued)

FOREIGN PATENT DOCUMENTS

| | | |
|---|---|---|
| EP | 0450186 | 10/1991 |
| WO | WO 2012/170732 | 12/2012 |

OTHER PUBLICATIONS

International Search Report and Written Opinion from PCT/US2022/014831, dated May 24, 2022, 11 pages.

*Primary Examiner* — Kevin C Sirmons
*Assistant Examiner* — Antarius S Daniel
(74) *Attorney, Agent, or Firm* — Dymera IP, LLC

(57) ABSTRACT

A drug delivery system including an implantable reservoir containing drug microspheres, with an innocuous fluid flushed through the implantable microsphere reservoir to form a drug containing solution for delivery within a body of a patient.

23 Claims, 7 Drawing Sheets

(51) Int. Cl.
*A61M 5/142* (2006.01)
*A61M 5/168* (2006.01)
*A61M 39/02* (2006.01)

(52) U.S. Cl.
CPC .... *A61M 5/16827* (2013.01); *A61M 39/0247* (2013.01); *A61M 2005/14284* (2013.01); *A61M 2039/0261* (2013.01); *A61M 2202/0007* (2013.01); *A61M 2202/04* (2013.01); *A61M 2205/50* (2013.01)

(58) Field of Classification Search
CPC ...... A61M 2205/582; A61M 2205/583; A61M 2205/7545; A61M 39/0208; A61M 39/04; A61M 39/12; A61M 5/1428; A61K 9/16
See application file for complete search history.

(56) References Cited

U.S. PATENT DOCUMENTS

| | | | | |
|---|---|---|---|---|
| 2006/0264911 | A1* | 11/2006 | Nelson | A61M 39/12 604/890.1 |
| 2007/0255237 | A1* | 11/2007 | Lobl | A61M 39/105 604/288.01 |
| 2013/0116665 | A1* | 5/2013 | Humayun | A61M 5/162 604/891.1 |
| 2013/0324969 | A1* | 12/2013 | Imran | A61M 5/14276 604/513 |
| 2016/0075776 | A1* | 3/2016 | Ashton | C07K 14/7151 424/134.1 |
| 2022/0133990 | A1* | 5/2022 | Bodner | A61M 5/162 604/288.01 |

* cited by examiner

IMPLANTABLE MICROSPHERE RESERVOIR

RELATED APPLICATION INFORMATION

The application claims the benefit of U.S. Provisional Application No. 63/148,661, filed Feb. 12, 2021, the contents of which are fully incorporated herein by reference.

TECHNICAL FIELD

The present technology is generally related to implantable medical devices, and more particularly to implantable drug delivery devices for managing the delivery and dispensation of prescribed therapeutic agents.

BACKGROUND

Recent developments in medical science have led to the development of new types of therapy in the treatment of debilitating tremor, spasms, chronic pain, cancer, and certain types of neurodegenerative diseases, including Huntington's disease, Spinal Muscular Atrophy (SMA), survival motor neuron (SMN) deficiency, amyotrophic lateral sclerosis (ALS), Angelman's Syndrome, Dravet Syndrome, Alzheimer's disease, progressive supranuclear palsy (PSP), frontotemporal dementia (FTD), Parkinson's Disease, central nervous system (CNS) lymphoma, and leptomeningeal cancer, among others. In many cases, treatment of these diseases and conditions may require administration of prescribed therapeutic agents into the intrathecal space of the patient according to a prescribed schedule. Traditional methods of accessing the intrathecal space include lumbar puncture.

Lumbar puncture (alternatively referred to as a "spinal tap") is the insertion of a needle into the spinal canal to provide access to the cerebrospinal fluid (CSF) that surrounds the brain and spinal cord. In a typical lumbar puncture procedure, local anesthesia is injected into the lumbar area of the back, and a long needle is inserted between the bones of the spine (vertebrae) to puncture through the dura mater and other tissues to enter the spinal canal. Sometimes radiographic imaging is employed to ensure proper placement of the needle.

Lumbar puncture carries certain exposure risks associated with deleterious side effects. Some of the risks include post-lumbar puncture headache, back discomfort or pain, bleeding, infection, and brainstem herniation. Repeated lumbar puncture, for example over the course of multiple prescribed therapies, expose the patient to these risks and complications each time the procedure is performed. Moreover, in part because of the heightened risks, a lumbar puncture procedure is typically performed by a physician (often a neurologist) in a surgical setting, which can present its own set of complications, including an increased cost to the procedure and potential delays where a qualified physician or facility is not available.

SUMMARY OF THE DISCLOSURE

The techniques of this disclosure generally relate to an implantable medical device, such as an implantable port, loaded with microspheres containing a therapeutic agent for intrathecal delivery into a patient. In embodiments, intrathecal delivery of the therapeutic agent can be affected by percutaneously injecting an innocuous fluid (e.g., saline solution or artificial CSF) into a portion of the implantable medical device. As the injected fluid flows through the implantable medical device, the therapeutic agent eludes from the microspheres into the fluid until an equilibrium concentration is reached. Further injection of fluid into the implantable medical device causes the therapeutic agent containing fluid to be displaced by incoming fluid, so as to affect a delivering flow of the therapeutic agent into the intrathecal space or other targeted drug delivery sites (e.g., intracranial space, vasculature, etc.) of the patient.

The systems, devices and methods disclosed herein provide a number of advantages over traditional lumbar puncture techniques. In particular, embodiments of the present disclosure significantly reduce patient exposure to the complications and risks associated with a prescribed series of lumbar puncture procedures, by limiting penetration of the dura matter to a one-time placement of an intrathecal catheter. Thereafter, multiple administrations of the therapeutic agent can be performed by any person qualified to perform a simple percutaneous injection, including the patient. Moreover, because an innocuous fluid such as a saline solution, artificial CSF or any other generally harmless, non-drug containing fluid is used, there is little to no risk of inadvertently injecting the therapeutic agent directly into the subcutaneous pocket surrounding the port, which is a risk associated with implanted ports. Rather, because the therapeutic agent eludes from the microspheres over a period of time until an equilibrium concentration is reached, the risk of an accidental overdose is significantly reduced. That is, because of the time release of the microspheres, injection of larger than prescribed amounts of fluid generally result in a diluted concentration of therapeutic agent (e.g., fluid that has not reached an equilibrium concentration of therapeutic agent) flowing into the intrathecal space.

Encapsulating the therapeutic agent in microspheres enables a large quantity of therapeutic agent to be packed into a relatively small enclosure, thereby enabling the administration of many doses of therapeutic agent from the implantable medical device. For example, in some embodiments, microspheres can carry between about 25 to about 50 times more therapeutic agent than a liquid-based equivalent. When the supply of therapeutic agent is exhausted (or near to exhaustion), the relatively small size of the implantable medical device enables subcutaneous replacement of the implantable medical device on an outpatient basis. Moreover, a sutureless connector between the implantable medical device and the intrathecal catheter can enable continued use of the previously implanted intrathecal catheter over the lifetime of several implantable medical devices, so as to avoid the risks and complications associated with further lumbar puncture procedures.

One embodiment of the present disclosure provides a drug delivery system, including an implantable reservoir containing drug microspheres, wherein an innocuous fluid is flushed through the implantable microsphere reservoir to form a drug containing solution for delivery within a body of a patient.

In one embodiment, the drug microspheres release drug into the innocuous fluid until the drug containing solution reaches an equilibrium concentration in which further release of the drug ceases. In one embodiment, the drug delivery system further includes a catheter connector configured to enable the implantable medical device to be selectively coupled to a catheter implanted within the body of the patient. In one embodiment, the drug delivery system further includes an innocuous fluid receptacle port configured to receive a subcutaneous injection of innocuous fluid. In one embodiment, the innocuous fluid receptacle port includes one or more positional marker. In one embodiment, the innocuous fluid receptacle port includes one or more needle detection sensor.

Another embodiment of the present disclosure provides an implantable medical device, including a fluid receptacle port configured to receive a percutaneous injection of an innocuous fluid, a microsphere reservoir fluidly coupled to the fluid receptacle port, the microsphere reservoir configured to enable therapeutic agent microspheres to dissolve into the innocuous fluid to form a therapeutic agent solution, and an access port fluidly coupled to the microsphere reservoir, the access port configured to enable sampling of the therapeutic agent solution prior to delivery to a targeted delivery site within a body of a patient.

In one embodiment, the implantable medical device further includes a catheter connector configured to enable the implantable medical device to be selectively coupled to a catheter implanted within the body of the patient. In one embodiment, the fluid receptacle port includes a self-sealing septum. In one embodiment, the fluid receptacle port comprises one or more positional marker. In one embodiment, the one or more positional marker comprises at least one of a light emitting diode, an acoustic device, a wireless location/orientation sensor, or a combination thereof as an aid in properly positioning a needle of a percutaneous injection device within the fluid receptacle port.

In one embodiment, the fluid receptacle port comprises one or more needle detection sensor. In one embodiment, the one or more needle detection sensor comprises at least one of a mechanical switch, resonant circuit, ultrasonic transducer, voltmeter, ammeter, ohmmeter, pressure sensor, flow sensor, capacitive probe, acoustic sensor, optical sensor, or combination thereof configured to detect a presence of a needle of a percutaneous injection device within the fluid receptacle port. In one embodiment, the implantable medical device further includes one or more physiological sensor. In one embodiment, the physiological sensor comprises at least one of a heart rate sensor, respiratory sensor, pulse oximeter, blood pressure sensor, intracranial pressure sensor, cerebrospinal fluid pressure sensor, intra-abdominal pressure sensor, temperature sensor, or combination thereof.

In one embodiment, the implantable medical device further includes a transceiver circuit configured to wirelessly receive information from and transmit information to at least one of an external programmer or server. In one embodiment, the implantable medical device further includes a clock/calendar element and an alarm drive configured to activate one or more notifications, alerts, or alarms. In one embodiment, the implantable medical device further includes a memory configured to maintain an access log of the fluid receptacle port. In one embodiment, the implantable medical device further includes at least one flow sensor configured to monitor a flow of fluid through the implantable medical device. In one embodiment, the implantable medical device further includes a first filter positioned upstream of the microsphere reservoir and a second filter positioned downstream of the microsphere reservoir. In one embodiment, the at least one of the first filter or second filter is configured to inhibit a flow of particles having a nominal diameter in a range of between about 1 μm and about 1000 μm.

Another embodiment of the present disclosure provides an implantable medical port, including an access port configured to receive a percutaneous injection of an innocuous fluid, and a microsphere reservoir fluidly coupled to the access port, the microsphere reservoir configured to enable therapeutic agent microspheres contained within the microsphere reservoir to dissolve into the innocuous fluid to form a therapeutic agent solution for delivery within a body of a patient.

In one embodiment, the microsphere reservoir at least partially surrounds the access port. In one embodiment, the implantable medical port further includes a catheter connector configured to enable the implantable medical device to be selectively coupled to a catheter implanted within the body of the patient. In one embodiment, the fluid receptacle port includes one or more positional marker. In one embodiment, the fluid receptacle port includes one or more needle detection sensor. In one embodiment, the implantable medical port further includes one or more physiological sensor. In one embodiment, the implantable medical port further includes a clock/calendar element and an alarm drive configured to activate one or more notifications, alerts, or alarms. In one embodiment, the implantable medical port further includes at least one flow sensor configured to monitor a flow of fluid through the implantable medical device.

Another embodiment of the present disclosure provides an implantable medical device, including a microsphere reservoir configured to contain therapeutic agent microspheres, and a pumping mechanism configured to flush cerebrospinal fluid through the medicament containing reservoir to enable the therapeutic agent microspheres contained within the microsphere reservoir to dissolve into the cerebrospinal fluid to form a therapeutic agent solution for delivery within a body of a patient.

In one embodiment, the pumping mechanism is in the form of a manually operated bulb. In one embodiment, the implantable medical device is selectively couplable to an inlet catheter and an outlet catheter, respectively positioned upstream and downstream of the microsphere reservoir. In one embodiment, the implantable medical device further includes one or more physiological sensor. In one embodiment, the implantable medical device further includes a clock/calendar element and alarm drive configured to activate one or more notifications, alerts, or alarms. In one embodiment, the implantable medical device further includes at least one flow sensor configured to monitor a flow of fluid through the implantable medical device.

Another embodiment of the present disclosure provides an implantable medical system, including an implantable microsphere reservoir configured to contain therapeutic agent microspheres, and an implantable pump in fluid connection with the implantable microsphere reservoir, the implantable pump configured to pump an innocuous fluid through the implantable microsphere reservoir to enable the therapeutic agent microspheres contained within the microsphere reservoir to dissolve or elude into the innocuous fluid to form a therapeutic agent solution for delivery within a body of a patient.

In one embodiment, the implantable pump includes a reservoir and a refill port, the refill port in fluid communication with the reservoir and configured to receive a percutaneous supply of innocuous fluid. In one embodiment, the implantable microsphere reservoir includes a catheter connector configured to enable the implantable medical device to be selectively coupled to a catheter implanted within the body of the patient. In one embodiment, the refill port comprises one or more positional marker. In one embodiment, the refill port comprises one or more needle detection sensor. In one embodiment, the implantable medical system further includes one or more physiological sensor. In one embodiment, the implantable medical system further includes a clock/calendar element and an alarm drive configured to activate one or more notifications, alerts, or alarms. In one embodiment, the implantable medical system further includes at least one flow sensor configured to monitor a flow of fluid through the implantable microsphere reservoir.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which.

Figure 1:
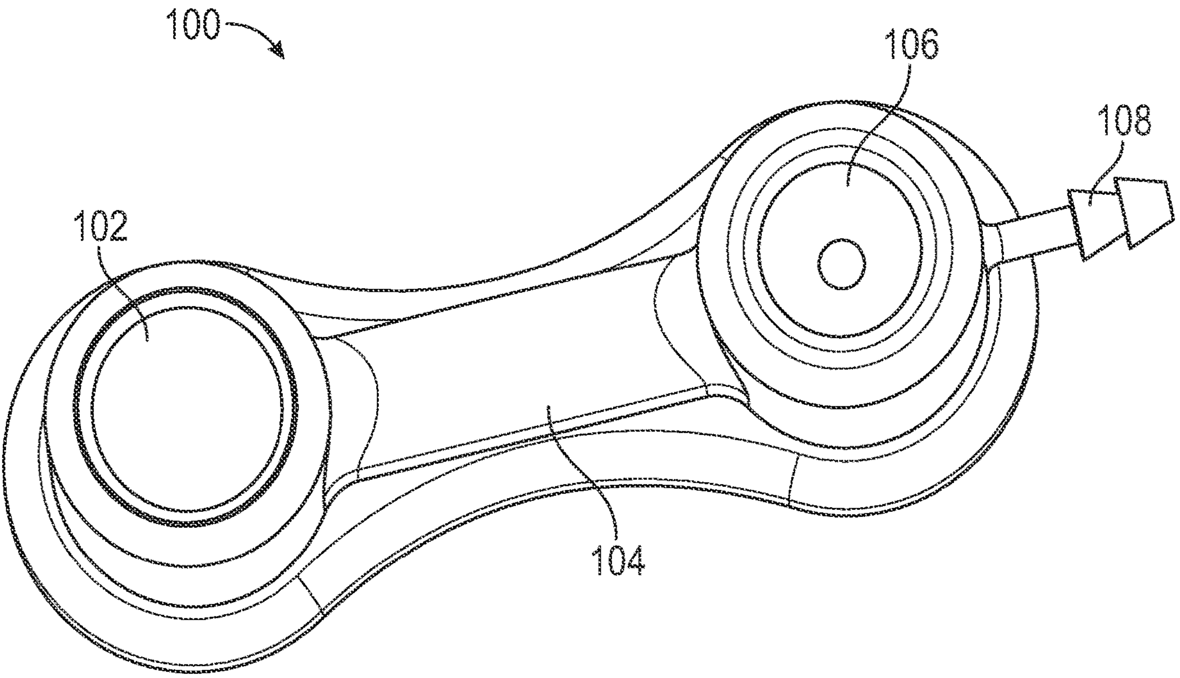
FIG. 1 is a perspective view depicting an implantable medical device configured to enable targeted delivery of a therapeutic agent via an implantable therapeutic agent microsphere containing reservoir, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Implantable medical devices, such as implantable medical pumps and ports, are useful in managing the delivery and dispensation of prescribed agents, nutrients, drugs, infusates such as antibiotics, blood clotting agents, analgesics and other fluid or fluid like substances (collectively "therapeutic agents" or "infusates") to patients in volume- and time-controlled doses as well as through boluses. Such implantable medical devices are particularly useful for treating diseases and disorders that require regular or chronic (i.e., long-term) pharmacological intervention, including pain, tremor, spasticity, certain types of neurodegenerative diseases, and other conditions, such as urinary or fecal incontinence, sexual dysfunction, obesity, and gastroparesis, to name just a few. Depending upon their specific designs and intended uses, implantable medical devices are well adapted to administer therapeutic agents to specific areas within the vasculatures and central nervous system, including the subarachnoid, epidural, intrathecal, and intracranial spaces, as well as to provide access to those spaces for aspiration.

Providing access to the cerebrospinal fluid for the administration of therapeutic agents or aspiration of fluid has a number of important advantages over other forms of therapeutic agent administration. For example, oral administration is often not workable because the systematic dose of the substance needed to achieve the therapeutic dose at the target site may be too large for the patient to tolerate without adverse side effects. Also, some substances simply cannot be absorbed in the gut adequately for a therapeutic dose to reach the target site. Moreover, substances that are not lipid soluble may not cross the blood-brain barrier adequately if needed in the brain. Further, implantable medical devices avoid the problem of patient noncompliance, namely the patient failing to take the prescribed drug or therapy as instructed.

Such implantable medical devices are typically implanted at a location within the body of a patient and are connected to a catheter configured to deliver therapeutic agent to a selected delivery site in the patient. The catheter is generally configured as a flexible tube with a lumen running the length of the catheter to a selected delivery site in the body, such as a targeted vascular, intracranial or subarachnoid site within the patient.

Implantable medical devices of this type often include a therapeutic agent reservoir, which is accessible for refill or aspiration through an access port. During the refill process, it is important that the therapeutic agent not be inadvertently injected directly into the body of the patient. For example, if the portion of the refilling apparatus employed to deliver the therapeutic agent is not properly positioned within the access port, the therapeutic agent can be injected directly into a pocket surrounding the implantable medical device (occasionally referred to herein as a "pocket fill"). Pocket fill during refill of an implantable medical device generally presents one of the largest risks associated with targeted drug delivery, and has the potential to result in patient death.

Over the years, various approaches have been developed to reduce the likelihood of hazards associated with a pocket fill. Such approaches include using one or more positioning markers to improve identification of the access port, employing needle detection sensor technology to confirm proper placement of the refilling apparatus within the access port, employing reservoir volume sensing technology to provide confirmation of a flow of fluid into the reservoir during the refill process, etc. Although these approaches have been effective in reducing the likelihood of hazards associated with an inadvertent pocket fill during the refill procedure, there is an ever present desire to further improve and enhance safety associated with targeted drug delivery. Embodiments of the present disclosure address this concern.

Referring to FIG. 1, an implantable medical device 100 configured to enable targeted delivery of a therapeutic agent via percutaneous injection of an innocuous fluid (e.g., saline solution, cerebrospinal fluid, or any other generally harmless, non-drug containing fluid) is depicted in accordance with an embodiment of the disclosure. Unlike conventional refill procedures, because an innocuous fluid is used, there is little to no risk of inadvertently injecting the therapeutic agent directly into the patient. Further, because there is little to no risk, infusion of the therapeutic agent can be performed by any person qualified to perform a simple, percutaneous injection, including the patient.

As the injected fluid flows through the implantable medical device, the microsphere contained within the implantable medical device dissolve or the therapeutic agent eludes from microspheres into the patient. Microspheres offer numerous advantages over traditional drug delivery methods, including prolonged therapeutic agent release rates (e.g., ranging from days to months), increased bio-protection of fragile therapeutics, and increased patient comfort and compliance. Microspheres can encapsulate many types of drugs, vaccines, antibiotics, and hormones, including small molecules, proteins and nucleic acids. Microspheres are generally represented as small monolithic spherical particles, with diameters in the micrometer range (e.g., having diameters in a range of about 1 μm to about 1000 μm).

Polymeric microspheres are generally composed of a biodegradable polymer matrix in which a therapeutic agent is distributed at the molecular or macroscopic level to enable a time-controlled release of the therapeutic agent to be tailored to the needs of a specific application. For example, some diseases may be most effectively treated by maintaining a relatively constant drug concentration within a target therapeutic range. Other types of treatments (e.g., antibiotics and vaccinations), may be most effectively delivered via bursts of the agent at specified intervals or in response to external stimuli. Moreover, controlled release of the therapeutic agent over longer periods of time can provide protection of therapeutic agents that may otherwise be destroyed by the body before their therapeutic effect can be realized. Further, prolonged release rates can replace a series of doses, potentially with a single dose, thus increasing patient comfort and compliance.

Possible microsphere materials include natural and synthetic polymer materials. For example, in some embodiments, the microsphere materials can be carbohydrates (e.g., agarose, carrageenan, chitosan10 starch, etc.), proteins (e.g., albumin, gelatin9, collagen, etc.), or chemically modified carbohydrates (e.g., poly dextran11, poly starch, etc.). In other embodiments, the microsphere material can be biodegradable polymers (e.g., lactides, glycolides & their co polymers, poly alkyl cyano acrylates, poly anhydrides, etc.) or nonbiodegradable polymers (e.g., acrolein, glycidyl methacrylate, tpoxy polymers PLGA (poly(D, L-lactide-co-glycolide)), PCA (poly(s-caprolactone)), PVA (poly(vinyl alcohol)), etc.). The therapeutic agent can be captured inside the microsphere (e.g., capsulated), dissolved into the matrix of the sphere, or attached to an outside of the sphere via one or more binding sites (e.g., ligands on the surface of the microsphere enabling proteins or biological agents to be attached to the microsphere). See also Microspheres for Controlled Release Drug Delivery, Neelesh K. Varde & Daniel W. Pack, Expert Opinion on Biological Therapy 4(1)(2004); and Microspheres as Drug Delivery System, B. Sree Gir Prasad, V. R. M Gupta, N. Devanna, & K. Jayasurya, Journal of Global Trends in Pharmaceutical Sciences, 5(3)(2014), the contents of which are incorporated by reference herein.

Encapsulating the therapeutic agent in microspheres enables a large quantity of therapeutic agent to be packed into a relatively small enclosure, thereby enabling the administration of many doses of therapeutic agent from the implantable medical device. For example, in some embodiments, microspheres can carry between about 25 to about 50 times more therapeutic agent than a liquid-based equivalent. Accordingly, in some implantable ports having a limited reservoir size, microspheres packed into the reservoir can carry about 32 times the amount of therapeutic agent that would otherwise fit into the reservoir if it were in a liquid form. Typical microsphere packing densities can range from about 40% to about 70% (with the remaining percentage being the space between microspheres).

With continued reference to FIG. 1, in some embodiments, the implantable medical device 100 can include a fluid receptacle portion 102, a microsphere reservoir portion 104, a catheter access port portion 106, and a catheter connector 108. Various embodiments of the present invention will be described in detail with reference to the drawings, wherein like reference numerals represent like parts and assemblies throughout the several views. Although specific examples of implantable medical ports and pumps are provided, it is to be appreciated that the concepts disclosed herein are extendable to other types of implantable devices. It is also to be appreciated that the term "clinician" refers to any individual that can prescribe and/or program a therapeutic regimen with any of the example embodiments described herein or alternative combinations thereof. Similarly, the term "patient" or "subject," as used herein, is to be understood to refer to an individual or object in which the therapy is to occur, whether human, animal, or inanimate. Various descriptions are made herein, for the sake of convenience, with respect to the procedures being performed by a clinician on a patient or subject (the involved parties collectively referred to as a "user" or "users") while the disclosure is not limited in this respect.

In operation, an innocuous fluid, such as a saline solution, can be introduced into the fluid receptacle portion 102, for example via a needle and syringe. As the innocuous fluid flows into the fluid receptacle portion 102, at least a portion of the innocuous fluid can flow into the microsphere reservoir portion 104. Within the microsphere reservoir portion 104, therapeutic agent from the microspheres can at least one of dissolve or elude into the innocuous fluid to form a therapeutic agent solution. In particular, the microspheres release therapeutic agent into the fluid until the solution reaches an equilibrium concentration of therapeutic agent, in which further distribution of the microspheres cease. Depending upon the design of the microspheres, reaching this equilibrium concentration may take many days, weeks or even months.

Thereafter, additional innocuous fluid introduced into the fluid receptacle portion 102 will displace fluid already in the implantable medical device 100, thereby pushing the therapeutic agent solution through the catheter access port portion 106, catheter connector 108, and into the patient (e.g., via a catheter terminating at a targeted delivery site). Because of the delay in incorporation of the therapeutic agent into the fluid (as a result of the time-controlled release of the therapeutic agent from the microspheres) and because further reaction of the microspheres cease upon reaching an equilibrium concentration of therapeutic agent in the fluid, the risk of an accidental overdose is significantly reduced. For example, where a larger than prescribed amount of fluid is forced through the fluid receptacle portion 102, the innocuous fluid will generally flow through the microsphere reservoir portion 104 at such a rate that only a small amount of therapeutic agent will be absorbed.

Figure 2:
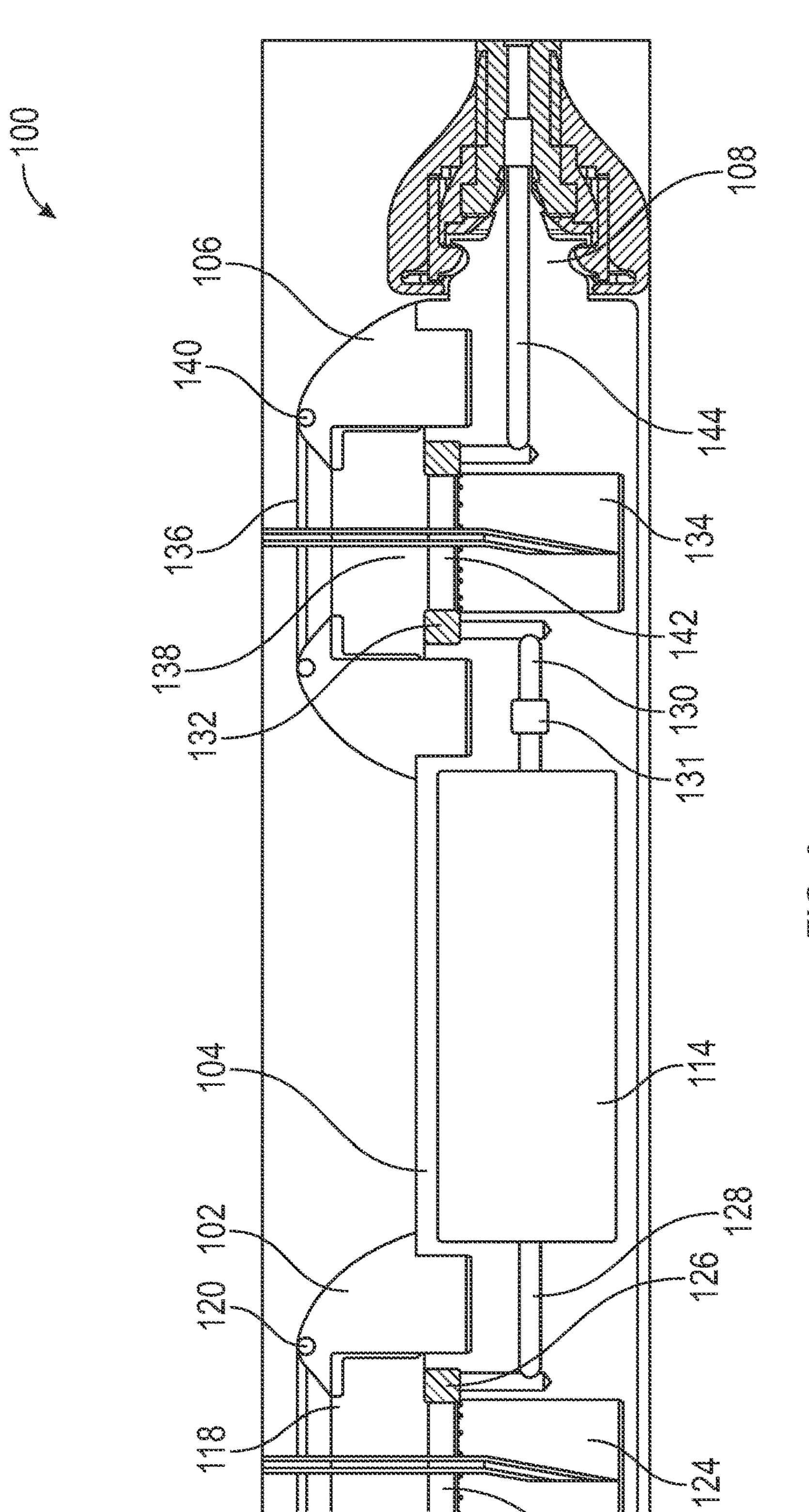
FIG. 2 is a cross-sectional view of the implantable medical device of FIG. 1.
Figure 3:
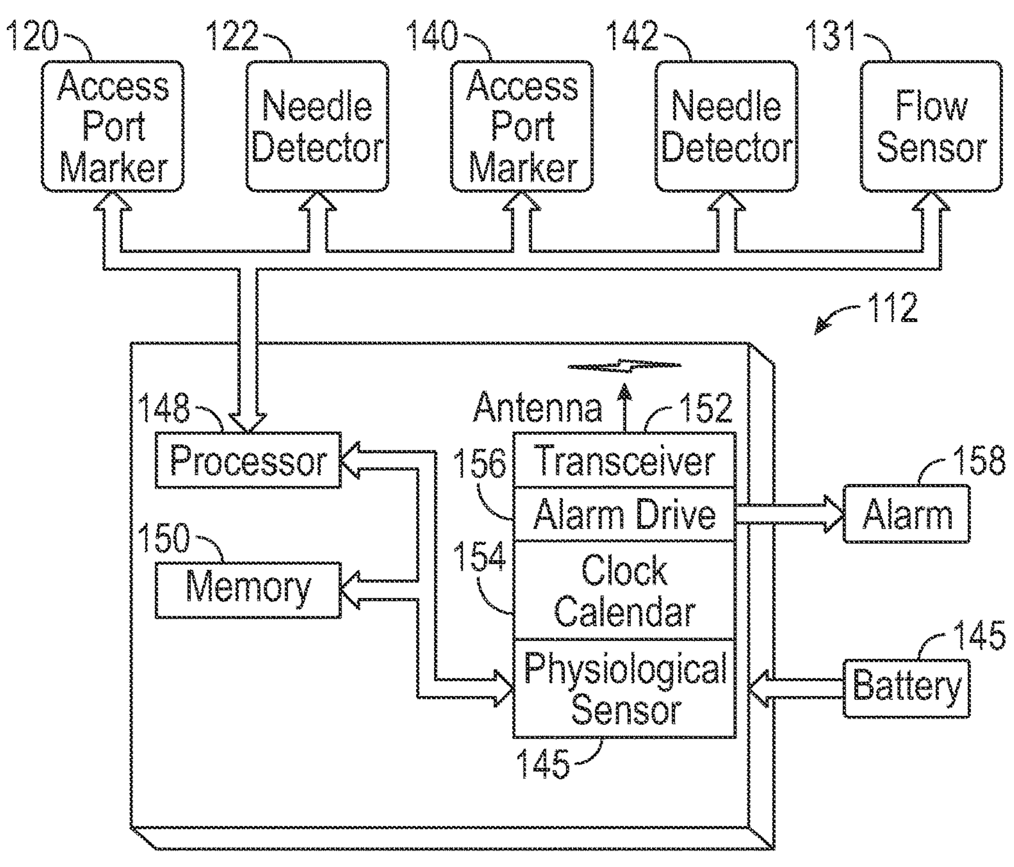
FIG. 3 is a block diagram of an implantable medical device configured to enable targeted delivery of a therapeutic agent via a microsphere containing reservoir, in accordance with an embodiment of the disclosure.

With additional reference to FIG. 2, a cross-sectional view of an implantable medical device 100 configured to enable targeted delivery of a therapeutic agent via a microsphere containing reservoir is depicted in accordance with an embodiment of the disclosure. In one embodiment, the implantable medical device 100 can include a housing 110, electrical circuitry 112 (as depicted in FIG. 3), and a microsphere reservoir 114. In some embodiments, housing 110 can generally form the fluid receptacle portion 102, microsphere reservoir portion 104 and catheter access port portion 106. In other embodiments, the various portions of the implantable medical device 100 can be formed separately. The housing 100 can be constructed of a material that is biocompatible and hermetically sealed, such as titanium, tantalum, stainless steel, plastic, ceramic, or the like.

The microsphere reservoir 114 can be carried by the housing 110, and can be configured to contain a quantity of therapeutic agent containing microspheres. Saline solution, CSF fluid, or the like can be introduced into the implantable medical device 100 via an access port 116, including a self-sealing septum 118 positioned beneath the skin of the patient. In some embodiments, the access port 116 can include one or more positional markers 120, for example in the form of a tactile protrusion or feedback mechanism, one or more lights or LEDs to illuminate through the tissue of the patient, an acoustic device to at least confirm a location of the access port 116, and/or one or more wireless location/orientation sensors to aid in positioning of a fluid delivery device relative to the implantable medical device 100. Additionally, in some embodiments, the access port 116 can include an optional needle detection sensor 122, for example in the form of a mechanical switch, resonant circuit, ultrasonic transducer, voltmeter, ammeter, ohmmeter, pressure sensor, flow sensor, capacitive probe, acoustic sensor, and/or optical sensor configured to detect and confirm the presence of an injection needle within the access port 116.

In some embodiments, fluid flowing into the access port 116 can fill an access port chamber 124. Additional fluid introduced into the access port chamber 124 can flow through a filter 126 and into a conduit 128 fluidly coupling the access port chamber 124 to the microsphere reservoir 114, where the fluid can mix with the therapeutic agent containing microspheres to form a therapeutic agent solution. As additional fluid is introduced into the implantable medical device 100, the therapeutic agent solution can flow through a second conduit 130, second filter 132, and into a catheter access port chamber 134. In some embodiments, the catheter access port chamber 134 can be accessed via an access port 136, including a self-sealing septum 138, thereby enabling a portion of the therapeutic agent solution to be extracted for analysis (e.g., to monitor a concentration of the therapeutic agent within the solution). Other potential uses of the catheter access port chamber 134 include checking a patency of an associated delivery route, sampling fluid (e.g., cerebrospinal fluid, etc.) from the patient, or to introducing other infusates into the implantable medical device 100 for targeted delivery within a patient. In some embodiments, the catheter access port 136 can include one or more positional markers 140 and/or one or more needle detection sensors 142. Excess therapeutic agent solution can continue to flow through the filter 132 into a third conduit fluidly coupling be catheter access port chamber 134 to the catheter connector 108 for targeted delivery within the body of the patient.

Referring to FIG. 3, a block diagram of an implantable medical device 100 configured to enable targeted delivery of a therapeutic agent via a microsphere containing reservoir is depicted in accordance with an embodiment of the disclosure. The electrical circuitry 112 can be carried in the housing 110 and can be powered by a power source 144. The power source 144 can be a battery, such as a rechargeable lithium-ion battery, or other power source such as an induction coil. The electrical circuitry 112 can include one or more optional physiological sensors 146, processor 148, memory 150, and transceiver circuitry 152. The one or more optional physiological sensors 146 can include a heart rate sensor, respiratory sensor, pulse oximeter, blood pressure sensor, intracranial pressure sensor, cerebrospinal fluid pressure sensor, intra-abdominal pressure sensor, temperature sensor, or the like.

The processor 148 can be a microprocessor, logic circuit, Application-Specific Integrated Circuit (ASIC) state machine, gate array, controller, or the like. The transceiver circuitry 152 can be configured to receive information from and transmit information to an external programmer and server through well-known techniques such as wireless telemetry, Bluetooth, or one or more proprietary communication schemes (e.g., Tel-M, Tel-C, etc.). In some embodiments, the electrical circuitry 112 can further include a clock/calendar element 154 configured to maintain system timing, and an alarm drive 156 configured to activate one or more notification, alert or alarm features, such as an illuminated, auditory or vibratory alarm 158.

In embodiments including one or more access port markers 120/140 or needle detection sensors 122/142, the processor 148 can be in electrical communication with the access port markers 120/140 and/or needle detection sensors 122/142, thereby enabling a record of fluid access to the respective access port chambers 124/134. In some embodiments, the implantable medical device 100 can be configured to keep an access log to the access port chambers 124/134, which can be stored for later recall by memory 150. In some embodiments, a quantity of remaining therapeutic agent within the microsphere reservoir 114 can be determined by the number of times that the access port chamber 124 has been accessed. In other embodiments, a quantity of remaining therapeutic agent can be determined by recording a flow of fluid through the implantable medical device 100, for example via flow sensor 131 (as depicted in FIG. 2).

Figure 4:
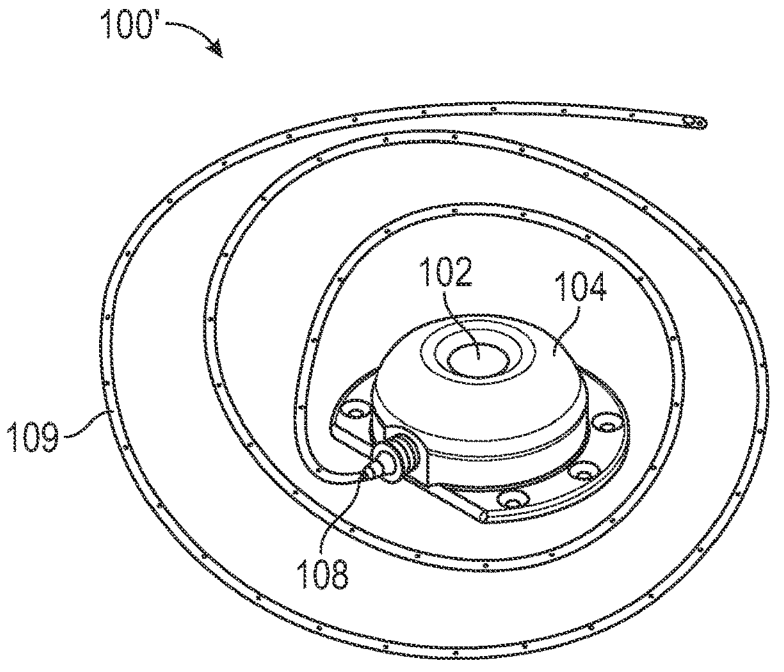
FIG. 4 is a perspective view of a compact implantable medical device configured to administer a therapeutic agent via a microsphere containing reservoir, in accordance with an embodiment of the disclosure.

Referring to FIG. 4, a compact implantable medical device 100' configured to administer a therapeutic agent via a microsphere containing reservoir is depicted in accordance with another embodiment of the disclosure. In some embodiments, the implantable medical device 100' can include a fluid receptacle portion 102 at least partially surrounded by a microsphere reservoir portion 104, which can be operably coupled to a catheter connector 108 and catheter 109 for delivery of a therapeutic agent solution to a target site within the body of the patient.

Figure 5:
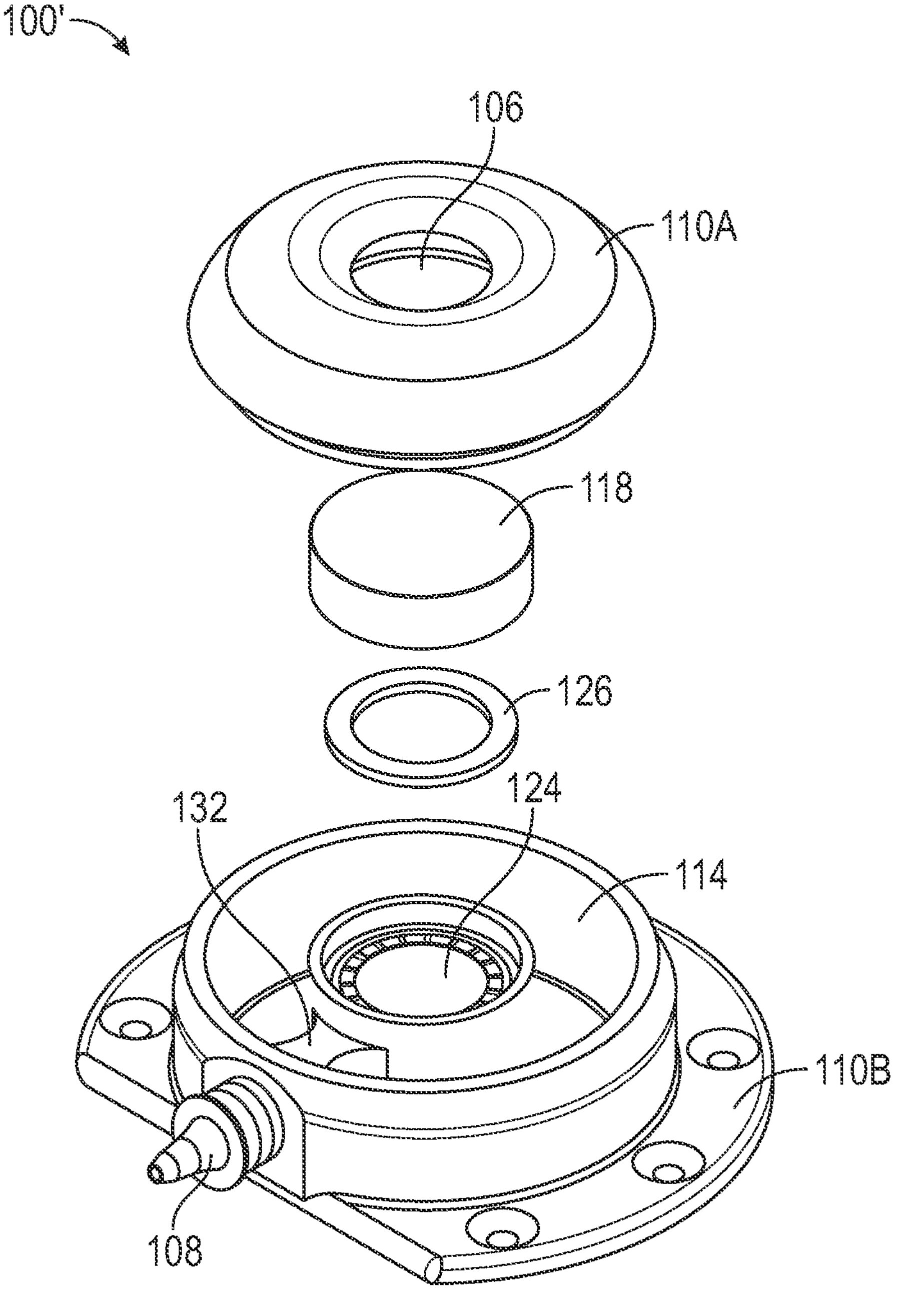
FIG. 5 is a partial, exploded perspective view of the compact implantable medical device of FIG. 4.
Figure 6:
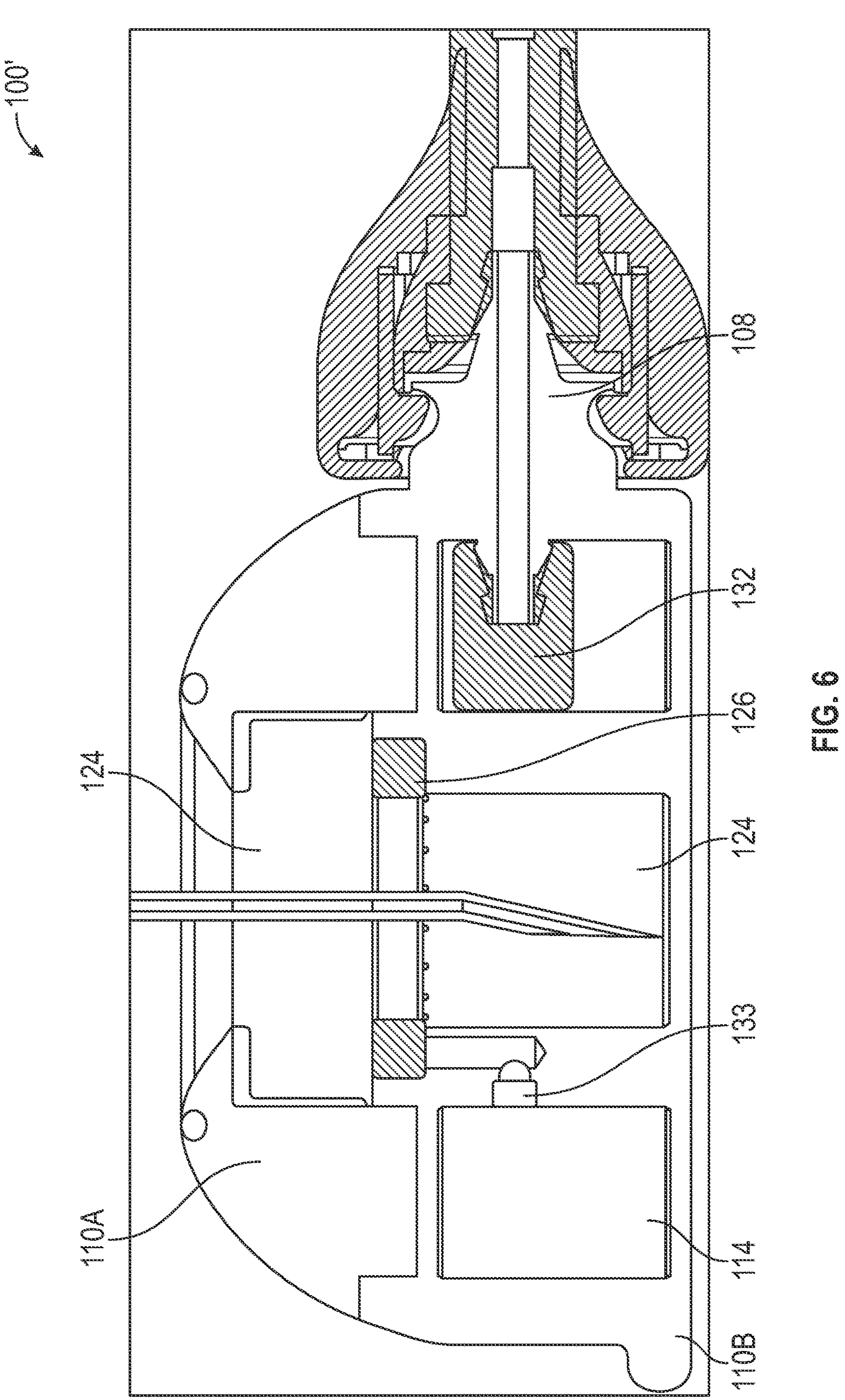
FIG. 6 is a cross-sectional view of the implantable medical device of FIG. 5.

With additional reference to FIGS. 5-6, perspective, exploded and cross-sectional views of the compact implantable medical device 100' of FIG. 4 are depicted in accordance with an embodiment of the disclosure. In one embodiment, the implantable medical device can include a housing 110, for example including a first portion 110A and a second portion 110B, which can be constructed of a material that is biocompatible and hermetically sealed, such as titanium, tantalum, stainless steel, plastic, ceramic, or the like.

In some embodiments, a first portion of the housing 110A can define an access port 116, configured to enable an introduction of a saline solution, cerebrospinal fluid, or other innocuous fluid into the implantable medical device. In some embodiments, access port 116 can include a septum 118 with self-sealing properties, thereby enabling a needle or other fluid introduction mechanism to pierce the septum while maintaining a fluid impermeable seal upon removal of the needle. Fluid introduced into the access port 116 can enter an access port chamber 124. As additional fluid is introduced into the access port chamber 124, a portion of the fluid can flow through a filter 126 and into a microsphere reservoir 114 configured to house a quantity of therapeutic agent containing microspheres. Fluid entering the microsphere reservoir 114 can begin to mix with the therapeutic agent to form a therapeutic agent solution. As fluid continues to enter the microsphere reservoir 114, the therapeutic agent solution can flow through a second filter 132 to the catheter connector 108.

In some embodiments, the microsphere reservoir 114 can be configured to at least partially surround the access port chamber 124, thereby enabling a microsphere reservoir 114 configured to contain a large quantity of therapeutic agent, while still enabling a compact implantable medical device 100' design. The filters 126/132 positioned upstream and downstream of the microsphere reservoir can be configured to restrict the flow of particles between a range of about 1 μm to about 1000 μm; although other filter sizes are also contemplated. In some embodiments, the implantable medical device 100' can include a one-way check valve 133 configured to inhibit a back flow of therapeutic agent solution, for example to inhibit withdrawal of therapeutic agent through the access port 116.

In some embodiments, the implantable medical device 100' depicted in FIGS. 4-6 can include electrical circuitry, such as that described in FIG. 3. In other embodiments, the implantable medical device 100 can be configured as an entirely manually operated, potentially lower cost device with no electrical components.

Figure 7:
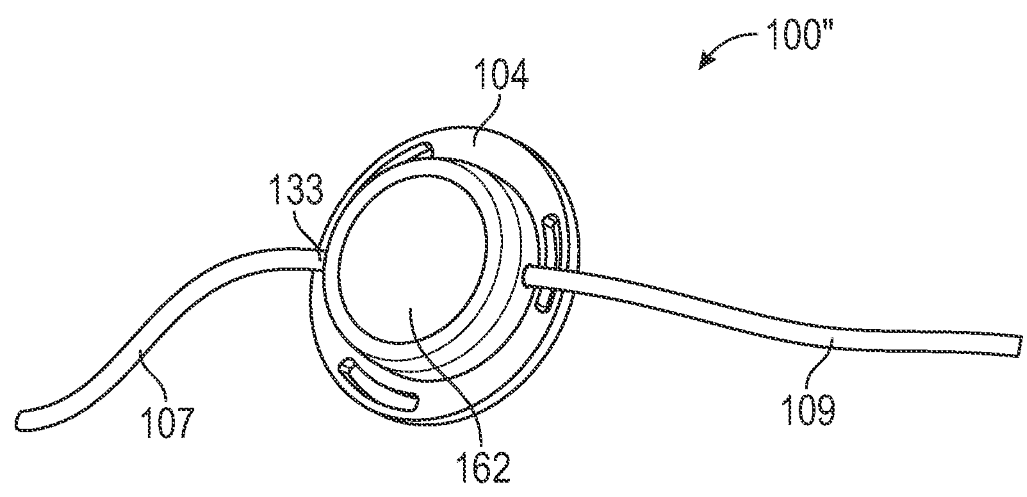
FIG. 7 is a perspective view of an implantable medical device configured to flush cerebrospinal fluid over a medicament containing reservoir, in accordance with an embodiment of the disclosure.

Referring to FIG. 7, a perspective view of an implantable medical device 100" configured to flush cerebrospinal fluid over a medicament containing reservoir is depicted in accordance with an embodiment of the disclosure. In some embodiments, the implantable medical device 100" can include an inlet catheter 107 and an outlet catheter 109 respectively positioned upstream and downstream of a microsphere reservoir portion 104, the inlet catheter 107 can be configured to enable bodily fluid from one area of the body to be pulled into the microsphere reservoir portion 104 for the generation of a therapeutic agent solution, while the outlet catheter 109 can enable delivery of the therapeutic agent solution to a targeted delivery site within the body of the patient.

In some embodiments, bodily fluid can be pulled into the microsphere reservoir portion 104 via a pumping mechanism 162. In some embodiments, the pumping mechanism 162 can be a manually operated bulb, configured to be operated through the skin of the patient. For example, in some embodiments, a user can depress and subsequently release a portion of the bulb 162, thereby creating a vacuum to draw fluid through the inlet catheter 107 and into the reservoir portion 104. Subsequently depressing the bulb 162 can force the therapeutic agent solution through the outlet catheter 109 for delivery of the therapeutic agent to the patient. In some embodiments, the implantable medical device 100" can include one or more check valves 133 to inhibit a back flow of the therapeutic agent upon actuation of the pumping mechanism 162. At the end of the serviceable lifetime, the reservoir portion 104 can be separated from the inlet and outlet catheters 107/109 for selective replacement and/or replenishment of the therapeutic agent containing microspheres.

In some embodiments, the implantable medical device 100" depicted in FIG. 7 can include electrical circuitry, such as that described in FIG. 3. For example, in some embodiments, a quantity of remaining therapeutic agent can be determined by recording a flow of fluid through the implantable medical device 100", for example via a flow sensor or other type of sensor configured to monitor actuation of the pumping mechanism 162. In other embodiments, the implantable medical device 100 can be configured as an entirely manually operated, potentially lower cost device with no electrical components.

Figure 8:
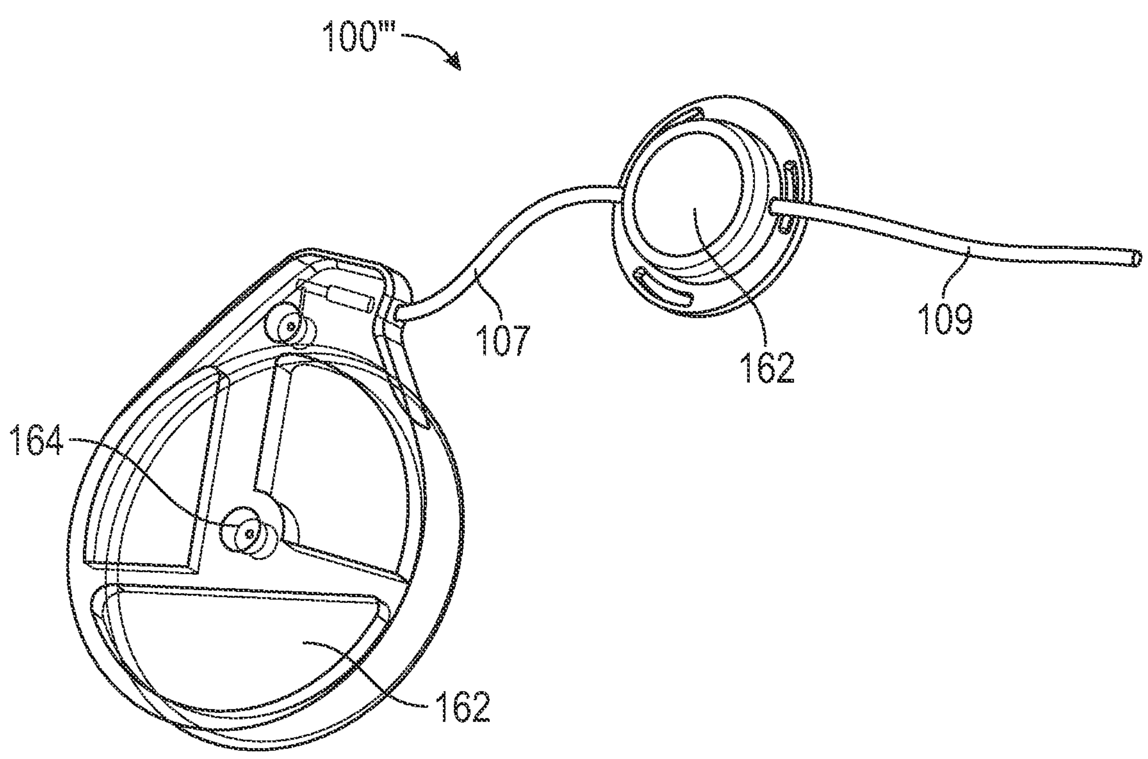
FIG. 8 is a perspective view of an implantable medical system configured to pump a saline solution or other innocuous fluid through a medicament containing reservoir, in accordance with an embodiment of the disclosure.

Referring to FIG. 8, a perspective view of an implantable medical system 100'" configured to pump a saline solution or other innocuous fluid through a medicament containing reservoir is depicted in accordance with an embodiment of the disclosure. In some embodiments, the implantable medical system 100'" can include a pumping mechanism 162, for example in the form of an implantable pump in fluid communication with the microsphere reservoir portion 104 via an inlet catheter 107. The implantable pump 162 can include a reservoir filled with an innocuous fluid (e.g., a saline solution, artificial CSF, etc.), and can be configured to push the innocuous fluid through the inlet catheter 107 into the reservoir portion 104. Fluid entering the reservoir portion 104 can mix with the therapeutic agent containing microspheres to form a therapeutic agent solution. Additional fluid pumped into the reservoir portion 104 can displace the therapeutic agent solution, thereby forcing the therapeutic agent solution out through the outlet catheter 109 and into the body of the patient.

Figure 9A:
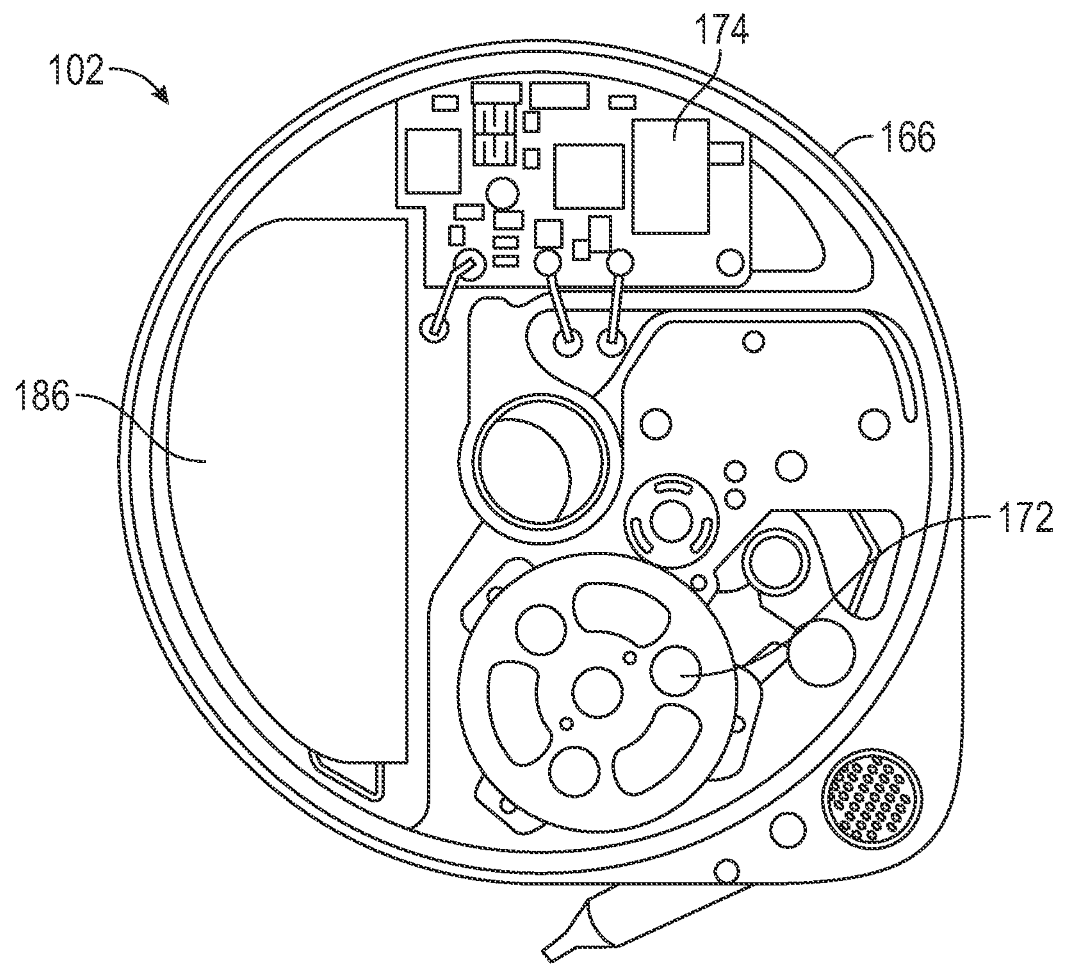
FIG. 9A is a top cross-sectional view depicting an implantable pump configured to pump a saline solution or other innocuous fluid through a medicament containing reservoir, in accordance with an embodiment of the disclosure.
Figure 9B:
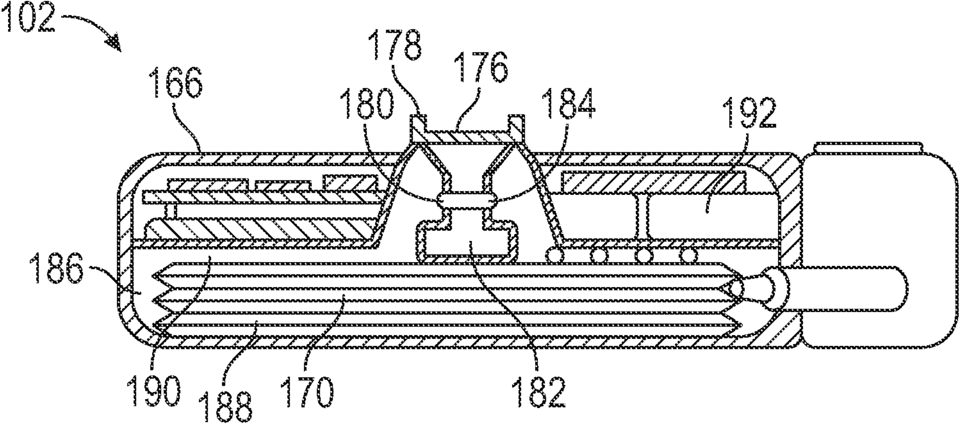
FIG. 9B is a side cross-sectional view depicting the implantable pump of FIG. 9A.

With additional reference to FIGS. 9A-B, cross-sectional views of an implantable pumping mechanism 162 configured to pump a saline solution or other innocuous fluid through a medicament containing reservoir is depicted in accordance with an embodiment of the disclosure. The implantable pump 162 can generally include a housing 166, power source 168, reservoir 170, pump 172, and computing device 174. The housing 166 can be constructed of a material that is biocompatible and hermetically sealed, such as titanium, tantalum, stainless steel, plastic, ceramic, or the like.

The reservoir 170 can be carried by the housing 166 and can be configured to contain an innocuous fluid, such as a saline solution, CSF or the like. In one embodiment, innocuous fluid within the reservoir 170 can be accessed via an access port 176. Accordingly, the access port 176 can be utilized to refill, aspirate, or exchange fluid within the reservoir 170. In some embodiments, the access port 176 can include one or more positional markers 178, for example in the form of a tactile protrusion or feedback mechanism, one or more lights or LEDs to illuminate through tissue of the patient, an acoustic device to at least confirm location of the access port 176, and/or one or more wireless location/orientation sensors to aid in positioning of a refilling device relative to the implantable pump 162.

In some embodiments, the access port 176 can include a septum 180 configured to seal a port chamber 182 relative to an exterior of the housing 166. The septum 180 can be constructed of a silicone rubber or other material having desirable self-sealing and longevity characteristics. The port chamber 182 can be in fluid communication with the reservoir 170. In one embodiment, the access port 176 can further include an optional needle detection sensor 184, for example in the form of a mechanical switch, resonant circuit, ultrasonic transducer, voltmeter, ammeter, ohmmeter, pressure sensor, flow sensor, capacitive probe, acoustic sensor, and/or optical sensor configured to detect and confirm the presence of an injection needle of a refilling apparatus.

The reservoir 170 can include a flexible diaphragm 186. The flexible diaphragm 186, alternatively referred to as a bellows, can be substantially cylindrical in shape and can include one or more convolutions configured to enable the flexible diaphragm 186 to expand and contract between an extended or full position and an empty position. In one embodiment, the flexible diaphragm 186 can divide the reservoir 170 into a fluid chamber 188 containing fluid (within the flexible diaphragm 186), and a vapor chamber 190 (surrounding the flexible diaphragm 186).

As the fluid chamber 188 is filled with an innocuous fluid, the flexible diaphragm 186 extends downwardly (with reference to FIG. 2B) toward a bottom portion of the housing 166 until it has reached a maximum volume or some other desired degree of fullness. Alternatively, as the fluid chamber 188 is aspirated, the flexible diaphragm 186 contracts upwardly toward a top portion of the housing 166 until the fluid chamber reaches a minimum volume. In one embodiment, the flexible diaphragm 186 can have a compression spring rate which tends to naturally bias the flexible diaphragm 186 towards an expanded position.

In one embodiment, the pumping mechanism 162 can optionally include a reservoir volume sensor 192, for example in the form of an inductance coil, capacitive probe, pressure sensor, acoustic sensor, and/or optical sensor/infrared (IR) transducer configured to detect the expansion/contraction of the flexible diaphragm 186. Accordingly, the fill sensor 192 can be utilized to measure a dimension of the reservoir 170 for the purpose of confirming a flow of fluid into the reservoir 170 during a refill procedure and/or determining a quantity of fluid pumped through the implantable pump 162 in order to infer a remaining therapeutic agent within the implantable medical system 100'''. The use of other types of sensors, including a flow sensor in order to estimate a remaining amount of therapeutic agent is also contemplated.

The pump 172 can be carried by the housing 166. The pump 172 can be in fluid communication with the reservoir 170 and can be in electrical communication with the computing device 174. The pump 172 can be any pump sufficient for pumping fluid, such as a peristaltic pump, piston pump, a pump powered by a stepper motor or rotary motor, a pump powered by an AC motor, a pump powered by a DC motor, electrostatic diaphragm, piezoelectric motor, solenoid, shape memory alloy, or the like In some embodiments, the implantable pump 162 can be programmed to selectively pump fluid through the reservoir 170 according to a prescribed schedule. Events associated with the pump, including the pumping of fluid can be logged for future use. Similar to previous embodiments, the reservoir portion 104 can be separated from the inlet and outlet catheters 107/109 for selective replacement and/or replenishment of the therapeutic agent containing microspheres.

The invention is further illustrated by the following embodiments:

A drug delivery system, comprising: an implantable reservoir containing drug microspheres, wherein an innocuous fluid is flushed through the implantable microsphere reservoir to form a drug containing solution for delivery within a body of a patient.

A system or method according to any embodiment, wherein the drug microspheres release drug into the innocuous fluid until the drug containing solution reaches an equilibrium concentration in which further release of the drug ceases.

A system or method according to any embodiment, further comprising a catheter connector configured to enable the implantable reservoir to be selectively coupled to a catheter implanted within the body of the patient.

A system or method according to any embodiment, further comprising a fluid receptacle port configured to receive a subcutaneous injection of innocuous fluid.

A system or method according to any embodiment, wherein the fluid receptacle port comprises one or more positional markers or tactile feedback mechanism.

A system or method according to any embodiment, wherein the fluid receptacle port comprises one or more needle detection sensors.

An implantable medical device, comprising: a fluid receptacle port configured to receive a percutaneous injection of an innocuous fluid; a microsphere reservoir fluidly coupled to the fluid receptacle port, the microsphere reservoir configured to enable therapeutic agent microspheres to at least one of dissolve or elude into the innocuous fluid to form a therapeutic agent solution; and an access port fluidly coupled to the microsphere reservoir, the access port configured to enable at least one of sampling of the therapeutic agent solution prior to delivery, checking a patency of a delivery route to a targeted delivery site within a body of a patient, sampling fluid from the patient, or delivering another agent.

A system or method according to any embodiment, further comprising a catheter connector configured to enable the implantable medical device to be selectively coupled to a catheter implanted within the body of the patient.

A system or method according to any embodiment, wherein the fluid receptacle port comprises a self-sealing septum.

A system or method according to any embodiment, wherein the fluid receptacle port comprises one or more positional markers or tactile feedback mechanism.

A system or method according to any embodiment, wherein the one or more positional markers comprise at least one of a light emitting diode, an acoustic device, a wireless location/orientation sensor, one or more tactile feedback mechanism, or a combination thereof as an aid in properly positioning a needle of a percutaneous injection device within the fluid receptacle port.

A system or method according to any embodiment, wherein the fluid receptacle port comprises one or more needle detection sensors.

A system or method according to any embodiment, wherein the one or more needle detection sensors comprise at least one of a mechanical switch, resonant circuit, ultrasonic transducer, voltmeter, ammeter, ohmmeter, pressure sensor, flow sensor, capacitive probe, acoustic sensor, optical sensor, or combination thereof configured to detect a presence of a needle of a percutaneous injection device within the fluid receptacle port.

A system or method according to any embodiment, further comprising one or more physiological sensors.

A system or method according to any embodiment, wherein the physiological sensors comprise at least one of a heart rate sensor, respiratory sensor, pulse oximeter, blood pressure sensor, intracranial pressure sensor, cerebrospinal fluid pressure sensor, intra-abdominal pressure sensor, temperature sensor, or combination thereof.

A system or method according to any embodiment, further comprising a transceiver circuit configured to wirelessly receive information from and transmit information to at least one of an external programmer or server.

A system or method according to any embodiment, further comprising a clock/calendar element and an alarm drive configured to activate one or more notifications, alerts, or alarms.

A system or method according to any embodiment, further comprising a memory configured to maintain an access log of the fluid receptacle port.

A system or method according to any embodiment, further comprising at least one flow sensor configured to monitor a flow of fluid through the implantable medical device.

A system or method according to any embodiment, further comprising a first filter positioned upstream of the microsphere reservoir and a second filter positioned downstream of the microsphere reservoir.

A system or method according to any embodiment, wherein the at least one of the first filter or second filter is configured to inhibit a flow of particles having a nominal diameter in a range of between about 1 μm and about 1000 μm.

An implantable medical port, comprising: an access port configured to receive a percutaneous injection of an innocuous fluid; and a microsphere reservoir fluidly coupled to the access port, the microsphere reservoir configured to enable therapeutic agent microspheres contained within the microsphere reservoir to at least one of dissolve or elude into the innocuous fluid to form a therapeutic agent solution for delivery within a body of a patient.

A system or method according to any embodiment, wherein the microsphere reservoir at least partially surrounds the access port.

A system or method according to any embodiment, further comprising a catheter connector configured to enable the implantable medical device to be selectively coupled to a catheter implanted within the body of the patient.

A system or method according to any embodiment, wherein the fluid receptacle port comprises one or more positional markers or tactile feedback mechanism.

A system or method according to any embodiment, wherein the fluid receptacle port comprises one or more needle detection sensors.

A system or method according to any embodiment, further comprising one or more physiological sensors.

A system or method according to any embodiment, further comprising a clock/calendar element and an alarm drive configured to activate one or more notifications, alerts, or alarms.

A system or method according to any embodiment, further comprising at least one flow sensor configured to monitor a flow of fluid through the implantable medical device.

An implantable medical device, comprising: a microsphere reservoir configured to contain therapeutic agent microspheres; and a pumping mechanism configured to flush cerebrospinal fluid through the medicament containing reservoir to enable the therapeutic agent microspheres contained within the microsphere reservoir to at least one of dissolve or elude into the cerebrospinal fluid to form a therapeutic agent solution for delivery within a body of a patient.

A system or method according to any embodiment, wherein the pumping mechanism is in the form of a manually operated bulb.

A system or method according to any embodiment, wherein the implantable medical device is selectively couplable to an inlet catheter and an outlet catheter, respectively positioned upstream and downstream of the microsphere reservoir.

A system or method according to any embodiment, further comprising one or more physiological sensors.

A system or method according to any embodiment, further comprising a clock/calendar element and an alarm drive configured to activate one or more notifications, alerts, or alarms.

A system or method according to any embodiment, further comprising at least one flow sensor configured to monitor a flow of fluid through the implantable medical device.

An implantable medical system, comprising: an implantable reservoir configured to contain therapeutic agent microspheres; and an implantable pump in fluid connection with the implantable microsphere reservoir, the implantable pump configured to pump and innocuous fluid through the implantable microsphere reservoir to enable the therapeutic agent microspheres contained within the microsphere reservoir to at least one of dissolve or elude into the innocuous fluid to form a therapeutic agent solution for delivery within a body of a patient.

A system or method according to any embodiment, wherein the implantable pump comprises a reservoir and a refill port, the refill port in fluid communication with the reservoir and configured to receive a percutaneous supply of innocuous fluid.

A system or method according to any embodiment, wherein the implantable reservoir comprising a catheter connector configured to enable the implantable medical device to be selectively coupled to a catheter implanted within the body of the patient.

A system or method according to any embodiment, wherein the refill port comprises one or more positional marker or tactile feedback mechanism.

A system or method according to any embodiment, wherein the refill port comprises one or more needle detection sensor.

A system or method according to any embodiment, further comprising one or more physiological sensor.

A system or method according to any embodiment, further comprising a clock/calendar element and an alarm drive configured to activate one or more notifications, alerts, or alarms.

A system or method according to any embodiment, further comprising at least one flow sensor configured to monitor a flow of fluid through the implantable microsphere reservoir.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An implantable medical device, comprising:

an access port configured to receive a percutaneous injection of an amount of innocuous fluid;

a fluid receptacle chamber fluidly coupled to the access port and configured to receive the percutaneous injection of the amount of innocuous fluid;

a microsphere reservoir comprising microspheres containing a quantity of therapeutic agent, the microsphere reservoir being fluidly coupled to the fluid receptacle chamber and configured to receive the amount of innocuous fluid, wherein the microspheres are configured to elude less than the quantity of the therapeutic agent into the amount of innocuous fluid to form a therapeutic agent solution having an equilibrium concentration of the therapeutic agent, and wherein further release of the therapeutic agent from the microspheres ceases upon reaching the equilibrium concentration; and a catheter access chamber between and fluidly coupled to the microsphere reservoir and a catheter connector, the catheter access chamber being configured to receive the therapeutic agent solution and enable at least one of sampling of the therapeutic agent solution prior to delivery, checking a patency of a delivery route to a targeted delivery site within a body of a patient, sampling fluid from the patient, or delivering another agent.

2. The implantable medical device of claim 1, wherein the catheter connector is fluidly coupled to a catheter implanted within the body of the patient for delivering the therapeutic agent solution.

3. The implantable medical device of claim 1, wherein the fluid receptacle chamber comprises a self-sealing septum.

4. The implantable medical device of claim 1, wherein the fluid receptacle chamber comprises one or more positional markers or tactile feedback mechanisms.

5. The implantable medical device of claim 4, wherein the one or more positional markers comprise at least one of: a light emitting diode, an acoustic device, a wireless location/orientation sensor, or a combination thereof, as an aid in properly positioning a needle of a percutaneous injection device within the fluid receptacle chamber.

6. The implantable medical device of claim 1, wherein the fluid receptacle chamber comprises one or more needle detection sensors.

7. The implantable medical device of claim 6, wherein the one or more needle detection sensors comprise at least one of: a mechanical switch, a resonant circuit, an ultrasonic transducer, a voltmeter, an ammeter, an ohmmeter, a pressure sensor, a flow sensor, a capacitive probe, an acoustic sensor, an optical sensor, or a combination thereof, configured to detect a presence of a needle of a percutaneous injection device within the fluid receptacle chamber.

8. The implantable medical device of claim 1, further comprising one or more physiological sensors.

9. The implantable medical device of claim 8, wherein the physiological sensors comprise at least one of: a heart rate sensor, a respiratory sensor, a pulse oximeter, a blood pressure sensor, an intracranial pressure sensor, a cerebrospinal fluid pressure sensor, an intra-abdominal pressure sensor, a temperature sensor, or a combination thereof.

10. The implantable medical device of claim 1, further comprising a transceiver circuit configured to wirelessly receive information from and transmit information to at least one of an external programmer or a server.

11. The implantable medical device of claim 1, further comprising a clock/calendar element and an alarm drive configured to activate one or more notifications, alerts, or alarms.

12. The implantable medical device of claim 1, further comprising a memory configured to maintain an access log of the fluid receptacle chamber.

13. The implantable medical device of claim 1, further comprising at least one flow sensor configured to monitor a flow of fluid through the implantable medical device.

14. The implantable medical device of claim 1, further comprising a filter positioned upstream of the microsphere reservoir and a second filter positioned downstream of the microsphere reservoir.

15. The implantable medical device of claim 14, wherein at least one of the first filter or the second filter is configured to inhibit a flow of particles having a nominal diameter in a range of between about 1 μm and about 1000 μm.

16. The implantable medical device of claim 1, wherein the therapeutic agent is encapsulated inside the microspheres, dissolved into a matrix of the microspheres, or attached to the microspheres via one or more binding sites.

17. The implantable medical device of claim 1, wherein the access port comprises one or more needle detection sensors.

18. An implantable medical port, comprising:

an access port configured to receive a percutaneous injection of an amount of innocuous fluid;

a fluid receptacle chamber fluidly coupled to the access port and configured to receive the percutaneous injection of the amount of innocuous fluid;

a microsphere reservoir comprising microspheres containing a quantity of therapeutic agent, the microsphere reservoir being fluidly coupled to the and fluid receptacle chamber and configured to receive the amount of innocuous fluid, wherein the microspheres are configured to elude less than the quantity of the therapeutic agent into the amount of innocuous fluid to form a therapeutic agent solution having an equilibrium concentration of the therapeutic agent in the fluid, and wherein further elution of the therapeutic agent from the microspheres ceases upon reaching the equilibrium concentration;

a catheter access chamber fluidly coupled to the microsphere reservoir, the catheter access chamber being configured to receive the therapeutic agent solution from the microsphere reservoir; and a catheter connector fluidly connected to the catheter access chamber and configured to enable the implantable medical port to be selectively coupled to a catheter implanted within a body of a patient, wherein the catheter access chamber is configured to enable at least one of sampling of the therapeutic agent solution prior to delivery within the body of the patient, checking a patency of a delivery route to a targeted delivery site within the body of the patient, sampling fluid from the patient, or delivering another agent, and wherein a risk of an accidental overdose due to percutaneous injection of an excess amount of innocuous fluid through the access port is reduced because only a small additional amount of the therapeutic agent is eluded into the excess amount of innocuous fluid that flows through the microsphere reservoir until the equilibrium concentration of the therapeutic agent is reached in the excess amount of innocuous fluid.

19. The implantable medical port of claim 18, wherein the catheter connector is fluidly coupled to a catheter implanted within the body of the patient for delivering the therapeutic agent solution.

20. The implantable medical port of claim 18, wherein the therapeutic agent is encapsulated inside the microspheres, dissolved into a matrix of the microspheres, or attached to the microspheres via one or more binding sites.

21. An implantable medical system, comprising:

an implantable microsphere reservoir comprising microspheres containing a quantity of therapeutic agent;

an implantable pump in fluid connection with the implantable microsphere reservoir, the implantable pump configured to pump an amount of innocuous fluid from a fluid receptacle chamber into the implantable microsphere reservoir, wherein the microspheres contained within the microsphere reservoir are configured to elude less than the quantity of the therapeutic agent into the innocuous fluid to form a therapeutic agent solution having an equilibrium concentration of the therapeutic agent, and wherein further dissolution or elution of the therapeutic agent from the microspheres ceases upon reaching the equilibrium concentration; and a catheter access chamber fluidly coupled to the implantable microsphere reservoir and a catheter connector, the catheter access chamber being configured to receive the therapeutic agent solution, the catheter connector being configured to enable the implantable medical system to be selectively coupled to a catheter implanted within a body of a patient, wherein the implantable pump comprises the fluid receptacle chamber reservoir and a refill port, and wherein the refill port is configured to enable at least one of sampling of the therapeutic agent solution prior to delivery within the body of the patient, checking a patency of a delivery route to a targeted delivery site within the body of the patient, sampling fluid from the patient, or delivering another agent.

22. The implantable medical system of claim 21, wherein the refill port is in fluid communication with the fluid receptacle chamber of the implantable pump and configured to receive the amount of innocuous fluid percutaneously.

23. The implantable medical system of claim 21, wherein the therapeutic agent is encapsulated inside the microspheres, dissolved into a matrix of the microspheres, or attached to the microspheres via one or more binding sites.

* * * * *